United States Patent [19]

Pettit et al.

[11] 4,306,071

[45] Dec. 15, 1981

[54] 1,4-BIS(2-HALOETHYL)-1,4-DIAZABICY-CLO[2.2.1]-HEPTANE DIHYDROGEN DIMALEATE AND SELECTED SALTS

[75] Inventors: George R. Pettit, Paradise Valley; Donald P. Gieschen, Tempe, both of Ariz.; William E. Pettit, Edmonton, Canada

[73] Assignee: The United States of America as represented by the Department of Health & Human Services, Washington, D.C.

[21] Appl. No.: 94,088

[22] Filed: Nov. 14, 1979

[51] Int. Cl.$^3$ ............................................. C07D 487/08
[52] U.S. Cl. .................................... 548/211; 544/358; 548/324
[58] Field of Search ................. 544/349; 548/324, 211

[56] References Cited

PUBLICATIONS

Fessler et al., "J. Med. Chem.", 12:542 (1969).
Pettit et al., "Chem. and Ind.", 1805 (1964).
Abraham et al., J. Med. Chem., 14:1141 (1971).
Pettit et al., "J. Org. Chem.", 34:2978 (1969).

*Primary Examiner*—Paul M. Coughlan, Jr.
*Attorney, Agent, or Firm*—John S. Roberts, Jr.

[57] ABSTRACT

1,4-Bis(2'-haloethyl)-1,4-diazabicyclo[2.2.1]-heptane derivatives, such as diperchlorate, dichloride, diacetate, dibenzoate, diascorbate, disalicylate, ditartrate, disaccharin, dihydrogen dimaleate, together with ethyl sulfonate and periodate.

4 Claims, No Drawings

1,4-BIS(2-HALOETHYL)-1,4-DIAZABICY-CLO[2.2.1]-HEPTANE DIHYDROGEN DIMALEATE AND SELECTED SALTS

The invention described herein was made in the course of work under a grant or award from the Department of Health, Education, and Welfare.

The present application relates to the preparation and use principally of the compound 1,4-bis(2'-chloroethyl)-1,4-diazabicyclo[2.2.1]heptane dihydrogen dimaleate. Additional salts which are described in the chart below are: diperchlorate, dichloride, diacetate, dibenzoate, diascorbate, disalicylate, ditartrate, disaccharin, dihydrogen dimaleate, together with ethyl sulfonate and periodate. The ethyl sulfonate salt has certain solubility advantages which are in the same order but less than the dimaleate salt. The periodate salt, however, has been found to be extremely explosive. In fact, comparatively speaking, the periodate salt is a most violent explosive.

The chart below describes the structure of these compounds and Table 1 lists tumor activity.

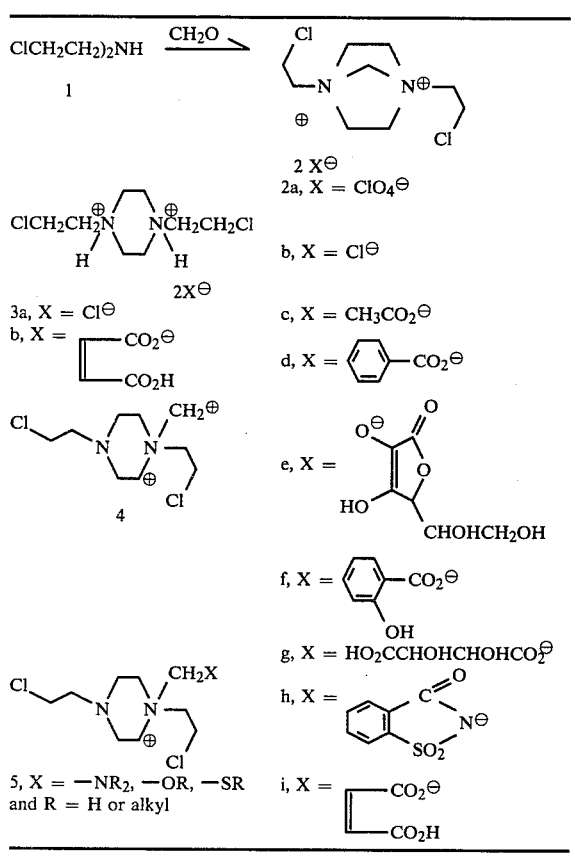

TABLE 1

| | Dose (mg/kg) | % T/C | % Cures |
|---|---|---|---|
| $X = ClO_4^\ominus$ (2a) | | | |
| P388 lympho-cyclic leukemia | 400 | 268 | 50 |
| | 200 | 190 | |
| | 100 | 154 | |
| | 50 | 145 | |
| L-1210 lymphoid leukemia | 150 | 190 | |
| | 100 | 189 | |
| | 66 | 154 | |
| | 44 | 140 | |
| Colon 38 | 400 | 47 | |
| | 200 | 62 | |
| Colon 26 | 400 | 271 | 60 |
| | 200 | 272 | 89 |
| | 100 | 175 | 30 |
| | 50 | 129 | |
| | 25 | 128 | |
| | 12.5 | 120 | |
| CD8F$_1$ mammary tumor | 400 | 6 | |
| | 200 | 24 | |
| | 100 | 44 | |
| | 50 | 57 | |
| | 25 | 104 | |
| | 12.5 | 65 | |
| Lewis lung carcinoma | 100 | 136 | |
| B16 melanocarcinoma | 100 | 146 | |
| | 50 | 116 | |
| | 25 | 136 | |
| Walker carcino-sarcoma | 80 | 562 | 100 |
| | 40 | 561 | 66 |
| | 20 | 237 | 33 |
| | 10 | 128 | 33 |
| | 5 | 128 | |
| $X = HO_2C-CH=CH-CO_2^\ominus$ (2i) | | | |
| P388 lympho-cyclic leukemia | 200 (toxic) | 192 | |
| | 100 | 146 | |
| | 50 | 123 | |
| | 25 | 113 | |
| L-1210 lymphoid leukemia | 200 | 180 | |
| | 100 | 148 | |
| | 50 | 120 | |
| | 25 | 90 | |
| | 12.5 | 100 | |
| Colon 38 | 100 | 45 | |
| | 50 | 44 | |
| | 25 | 78 | |
| | 12.5 | 84 | |
| Colon 26 | 200 | 186 | 20 |
| | 100 | 155 | 10 |
| | 50 | 133 | 10 |
| | 25 | 114 | 10 |
| | 12.5 | 102 | 10 |
| CD8F$_1$ mammary tumor | 400 | 0 | |
| | 200 | 4 | |
| | 100 | 19 | |
| | 50 | 78 | |
| | 25 | 85 | |
| | 12.5 | 16 | |
| B16 melanocarcinoma | 100 | 138 | |
| | 50 | 130 | |
| | 25 | 129 | |
| | 12.5 | 128 | |
| | 6.25 | 117 | |
| Ridgway osteogenic sarcoma | 200 | 121 | |
| | 100 | 124 | |
| | 50 | 110 | |
| | 25 | 94 | |
| Lewis lung carcinoma | 50 | 96 | |
| | 25 | 113 | |
| | 12.5 | 105 | |
| | 6.25 | 99 | |
| $X =$ (2h) | | | |
| P388 lympho-cyclic leukemia | 400 | 296 | 50 |
| | 200 | 240 | |

TABLE 1-continued

| | Dose (mg/kg) | % T/C | % Cures |
|---|---|---|---|
| | 100 | 198 | |
| | 50 | 171 | |
| Colon 26 | 400 | | 20 |
| | 200 | 171 | |
| | 100 | 134 | |
| | 50 | 116 | |
| | 25 | 106 | |
| CD8F$_1$ mammary | 600 | 12 | |
| tumor | 400 | 43 | |
| | 200 | 43 | |
| | 100 | 93 | |
| | 50 | 67 | |
| | 25 | 75 | |
| B16 melanocarcinoma | 200 | 143 | |
| | 100 | 120 | |
| | 50 | 117 | |
| | 25 | 108 | |

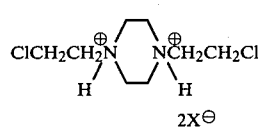

X = Cl
(3a)

| | | | |
|---|---|---|---|
| P388 lympho-cyclic leukemia | 2.0 (toxic) | | |
| | 1.0 | 167 | |
| | 0.50 | 145 | |
| | 0.25 | 120 | |
| | 0.10 | 110 | |
| L-1210 lymphoid leukemia | 2.0 | 97 | |
| | 1.0 | 154 | |
| | 0.50 | 145 | |
| | 0.25 | 125 | |
| | 0.12 | 110 | |

X = HO$_2$CCH=CHCO$_2^\ominus$
(3b)

| | | | |
|---|---|---|---|
| P388 lympho-cyclic leukemia | 0.30 (toxic) | | |
| | 0.20 | 111 | |
| | 0.10 | 116 | |
| | 0.05 | 102 | |
| L-1210 lymphoid leukemia | 0.20 | 125 | |
| | 0.10 | 110 | |
| | 0.05 | 102 | |
| Walker carcinosarcoma 256 | 0.15 | 39 | |
| | 0.075 | 85 | |
| | 0.037 | 78 | |

A type reaction to produce these salts which was disclosed in Fessler, et. al., *J. Med. Chem.*, 12:542 (1969), showed the preparation of the diperchlorate by condensing one mole of formaldehyde with 2 moles of bis(2-chloroethyl) amine to yield 1,4-bis(2'-chloroethyl)-1,4-diazabicyclo[2.2.1]heptane diperchlorate (2a), a compound exemplary of prior art compounds.

The present preferred variety is the dihydrogen dimaleate shown in the chart above as 2i. It is to be noted in contrast to the prior art compound, i.e., the perchlorate, that the present dimaleate for medicinal applications has a superior water-solubility contrasted with the perchlorate which is relatively insoluble. Secondly, the perchlorate is unstable, whereas the dimaleate is quite stable. Thirdly, the perchlorate is relatively toxic, whereas the data flowing from the maleate shows it to be relatively non-toxic. Additionally, the dichloride salt is also disclosed in *J. Med. Chem.*, 12:542 (1969), and this salt has been found to be unstable, whereas the maleate salt is stable.

It is noted that the diperchlorate is nowhere near as soluble in water; in fact, results show that it has 5% of the solubility that the dihydrogen dimaleate has. Furthermore, the dihydrogen dimaleate is as soluble as sucrose in water.

The 1,4-bis(2'-chloroethyl)-1,4-diazabicyclo-[2.2.1]heptane dication (2) has been found to exhibit remarkable antineoplastic activity. Detailed evaluation of dianion derivatives has shown a curative level of response against the murine P388 lymphocytic leukemia, colon 26, CD8F$_1$ mammary and the Walker 256 carcinosarcoma (rat) tumor systems. In addition, significant cancer chemotherapeutic activity was found using the murine L-1210 lymphoid leukemia, colon 38 and B16 melanocarcinoma. The bicyclo dication was first isolated, evaluated, and stored as the diperchlorate derivative (2a).

In the present application a preferred salt is the dihydrogen dimaleate derivative (2i).

PRIOR ART STATEMENT

Fessler, Pettit, and Settepani, "Antineoplastic Agents. XXV. 1,4-Diazabicyclo[2.2.1]heptanes," *J. Med. Chem.* 12:542 (1969).

Pettit and Settepani, "Condensation of Formaldehyde with N-Bis(2-Haloethyl)Amines: Structure of the Products," *Chem. and Ind.*, 1805 (1964).

Abraham, Rosenstein, and Pettit, "Structure of 1,4-Diazabicyclo[2.2.1]heptanes, a New Heterocyclic Ring System," *J. Med. Chem.*, 14:1141 (1971).

Pettit, Fessler, and Settepani, "1,4-Bis(2-chloroethyl)-1,4-diazabicyclo[2.2.1]heptane Diperchlorate," *J. Org. Chem.*, 34:2978 (1969).

GENERALIZED PROCEDURE

Since the objective of this investigation was to locate an anion such as that derived from ascorbic acid (Vitamin C) or another naturally occurring substance compatible with human utilization, a number of possibilities were examined. Ascorbic acid was especially attractive due to the possibility of increasing the immune response involved with interferon enhancement. The readily available maleic acid, a constituent of citrus and grape juices, and D-tartaric acid were to offer other useful choices. These three possibilities were inspected as part of a larger series of anions of decreasing nucleophilicity derived from the acids (pKa) acetic (4.74), benzoic (4.20), ascorbic (4.17), salicyclic (2.97), D-tartaric (2.93), maleic (2.0) and saccharin (1.60).

Two workable methods were found for displacing the perchlorate anions in (2a). The first was based upon the minimal solubility of potassium perchlorate in ethanol-acetonitrile mixtures and proved workable except with maleic and D-tartaric acids since their corresponding potassium salts were not sufficiently soluble in this solvent. However, the nucleophilicity of acetate, benzoate and ascorbate anions was sufficient to cause decomposition of substances 2c–e during isolation. While the disalicylate 2f was stable only in the cold, the disaccharin salt 2h was very conveniently obtained by this method and only slowly decomposed at ambient temperatures over a six-month period. At this point the potential carcinogenic (bladder) properties of saccharin became known and except for preliminary antineoplastic studies disaccharin salt (2h) was not further considered.

Ion exchange chromatography was utilized as a preferred method for displacing the perchlorate anions and in this way workable syntheses of ditartrate (2g) and the preferred dimaleate (2i) were realized. However, the ditartrate proved unstable at room temperature and could only be maintained at approximately −10°. The dihydrogen dimaleate (2i) proved quite stable at room temperatures and has been maintained under normal conditions without any detectable change for over 3 years.

EXPERIMENTAL

Distilled (in glass) water was employed in the ion exchange procedures. All other solvents were redistilled. Melting points were determined by the capillary method (oil bath) and were uncorrected. The infrared spectra (KBr) were recorded using a Perkin Elmer 299 spectrophotometer. Proton magnetic resonance ($^1$H nmr) spectra (δ in ppm with respect to tetramethylsilane or sodium 2,2-dimethyl-2-silapentane-5-sulfonate) were determined using Varian Associates T-60A or XL-100 instruments. The $^{13}$C nmr spectra (in ppm downfield from internal tetramethylsilane or p-dioxane, 67.4 ppm) were also measured (at 22.6 MHz) employing a Bruker WH-90 nmr spectrometer. All of the nmr spectra were determined in deuterium oxide solution unless otherwise noted. Elemental microanalyses were performed in the Spang Microanalytical Laboratory, Eagle Harbor, Mich.

EXAMPLE 1

Bis(2-chloroethyl)amine (1) Hydrochloride

Purification of currently available commercial specimens of nitrogen mustard hydrochloride proved less efficient than utilizing the following improved synthesis. A solution of thionyl chloride (520 ml or 860 g) in chloroform (460 ml) was slowly added through a dropping funnel to a solution of 2,2′-iminodiethanol (212 g, Aldrich Chemical Co.) in 600 ml of chloroform. The reaction mixture was contained in a 5-liter 3-necked round bottom flask equipped for efficient reflux, rapid mechanical stirring and a cold-water bath (for maintaining the reaction temperature at approximately 20°). When the viscous material that formed on the stirring blade reached a constant mass, the remaining thionyl chloride was rapidly added. The water bath was heated and the mixture was slowly (to minimize foaming) brought to reflux temperature. After approximately 30 min. the yellow solution became clear and was allowed to cool. The crystalline product was collected and washed successively with chloroform (3×125 ml) and diethyl ether (200 ml) to yield bis(2-chloroethyl)amine hydrochloride (250 g) as colorless crystals decomposing at 212°–214°. Two recrystallizations from 4:1 acetone-absolute ethanol provided the hydrochloride (140 g) as needles decomposing at the same temperature: ir, 2975, 2760, 2440, 1595, 1460, 1445, 1355, 1305, 1050, 1000, 960, 885, 860, 840, 785, 755, 700, and 675 cm$^{-1}$.

Recrystallization of bis(2-chloroethyl)amine hydrochloride obtained by this method was found unnecessary for the preparation of 1,4-bis(2′-chloroethyl)-1,4-diazabicyclo[2.2.1]heptane diperchlorate (2a).

EXAMPLE 2

1,4-bis(2′-chloroethyl)-1,4-diazabicyclo[2.2.1]heptane diperchlorate (2a)

The following procedure was found routinely convenient and reliable for the preparation of diperchlorate, 2a. A 10% sodium hydroxide solution (140 ml) was added in portions to bis(2-chloroethyl)amine hydrochloride (50.0 g) in 100 ml of water. The mixture was extracted with diethyl ether (100 ml and 2×50 ml) and the combined extract was washed with saturated sodium chloride solution and dried (ice-bath) over anhydrous magnesium sulfate. Solvent was removed by rotary evaporation (ice-bath temperature) to afford the thermally unstable bis(2-chloroethyl)amine as a colorless oil. Upon dissolution of the amine in absolute ethanol (150 ml), 37% formalin (50 ml) was quickly added. After one day at room temperature, the mixture was cooled (ice-bath) and 27 ml of 70% perchloric acid was slowly added. Crystallization of diperchlorate (2a) began within a few minutes and when complete 32.2 g of diperchlorate (2a) was collected and recrystallized from water-ethanol to afford colorless crystals (24.2 g) decomposing at 222°–223° [as found for the original elemental analytical sample (1)]: $^{13}$C nmr (deuterium oxide) 37.43 (-CH$_2$CH$_2$Cl), 59.73 (ring-CH$_2$CH$_2$-), 60.05 (-CH$_2$CH$_2$Cl), and 83.39 (ring-CH$_2$-).

EXAMPLE 3

1,4-bis(2′-chloroethyl)-1,4-diazabicyclo[2.2.1]heptane disaccharin (2h)

Freshly prepared (from saccharin and potassium hydroxide in water) potassium saccharin (29.2 g) was dissolved in 95% ethanol (900 ml) and the hot solution was rapidly poured into a solution of diperchlorate (2a) (28.1 g) in acetonitrile (200 ml). After 2.25 h the precipitate of potassium perchlorate was collected, the filtrate was concentrated to 150 ml and potassium perchlorate was again collected. The remaining acetonitrile solution was concentrated to a yellow oil which was dissolved in water and lyophilized to yield 37.4 g (96%) of pale yellow flakes: ir, 3460, 3100, 1725, 1610, 1405, 1360, 1315, 1125, 1065, 1025, 880, 835, 770, 735, 705, 660, 610 and 585 cm$^{-1}$; pmr δ4.16–4.41 (m, 8H), 4.48 (s, 8H), 5.66 (s, 2H), and 7.85 (s, 4H).

The infrared and especially the $^1$H-nmr spectra showing the methylene bridge signal at 5.66 δ were in complete accord with the assigned structure (2h). When stored at ambient temperatures in a sealed container, disaccharin (2h) underwent slow transformation. In approximately six months the original substance remained in only minor amount.

By employing the general procedure used to obtain disaccharin (2h), the following reactions were attempted in hot ethanol-acetonitrile solutions. In each case freshly prepared potassium acetate, benzoate, ascorbate, and salicylate were separately allowed to react with diperchlorate (2a). The minimal solubilities of dipotassium D-tartrate and maleate in ethanol-acetonitrile mixtures precluded their use in this synthetic approach. The diacetate (2c) and dibenzoate (2d) were rapidly destroyed during the isolation procedure. Diascorbate (2e) was partially transformed during isolation and further characterization proved impractical.

Reaction between potassium salicylate (12.4 g in 250 ml of 95% ethanol) and diperchlorate (2a) (15.0 g) in acetonitrile (200 ml) allowed nearly the theoretical amount of potassium perchlorate to be collected. Removal of solvent afforded a pale yellow oil that exhibited pmr (d$_3$-acetonitrile) δ 4.0–4.8 (complex, 16H), 5.25 (2, H$_2$O), 5.95 (s, 2H), 6.7–7.1, 7.2–7.5, and 7.8–8.1 (complex, aromatic). Various approaches to purifying disalicylate (2f) led to its rapid destruction and this was easily monitored by observing disappearance of the methylene bridge protons at 5.9 δ in the pmr spectra. Application of an ion exchange technique (cf. 2i) to preparation of the acetate, benzoate, and salicylate derivatives was also unsuccessful.

EXAMPLE 4

1,4-bis(2'-chloroethyl)-1,4-diazabicyclo[2.2.1]heptane dihydrogen dimaleate (2i)

In a typical experiment a 100 ml volume of Mallinckrodt Amberlite IRA-400 (chloride form) ion exchange resin in a chromatography column was treated with 40 volumes of 1 N sodium hydroxide per volume of resin. The resulting IRA-400 (hydroxide form) was washed with water until the eluate was neutral to Hydrion pH paper. The resin bimaleate was prepared by elution with 600 ml of 1 N maleic acid. The large excess of maleic acid was employed to allow conversion to the dihydrogen dimaleate (2i) rather than the monomaleate derivative. Excess acid was removed by a final elution with 200 ml of water. A solution of diperchlorate (2a) (20.0 g) in 1 liter of water was passed through the resin. Elution with 1.5 liter of water and lyophilization of the combined fractions afforded 18.2 g (85%) of dihydrogen dimaleate (2i). Three recrystallizations from ethanol provided an analytical specimen melting at 118°–119° (slight decomposition): $\nu$max 3440, 3010, 2920, 2850, 1580, 1495, 1385, 1365, 1195, 1110, 1070, 995, 875, 865, 750 and 695 cm$^{-1}$; pmr δ 4.16–4.41 (m, 8H), 4.47 (s, 8H), 5.68 (s, 2H), 6.32 (s, 2H).

Anal. Calcd for $C_{17}H_{24}Cl_2O_8N_2$: C, 44.85; H, 5.31; Cl, 15.57; O, 28.11; N, 6.15.

Found: C, 44.95; H, 5.36; Cl, 15.56; O, 27.99; N, 6.14.

The ion exchange technique utilized for obtaining dihydrogen dimaleate (2i) was analogously applied to the preparation of dihydrogen ditartrate (2g) from 20 g of diperchlorate (2a). The 1.5 liter water eluate upon lyophilization led to 20.2 g of glassy residue. The product was precipitated three times with diethyl ether from ethanol-water and a water solution was relyophilized to yield dihydrogen ditartrate (2g) as a very pale yellow powder: pmr δ 4.16–4.41 (m, 8H), 4.47 (s, 8H), 4.83 (s, 2H), 5.68 (s, 2H).

We claim:

1. 1,4-Bis(2'-chloroethyl)-1,4-diazabicyclo-[2.2.1]heptane dication where the dication is in conjunction with a dianion selected from one member of the group consisting of disaccharin, dihydrogen dimaleate, and ethyl sulfonate.

2. The compound of claim 1 wherein the dianion is disaccharin.

3. The compound of claim 1 wherein the dianion is dihydrogen dimaleate.

4. The compound of claim 1 wherein the dianion is ethyl sulfonate.

* * * * *